United States Patent [19]
Zivny

[11] Patent Number: 4,892,527
[45] Date of Patent: Jan. 9, 1990

[54] SPORTMAN'S REUSABLE, ANTI-COLLAPSING URINE COLLECTION DEVICE

[76] Inventor: Zbig Z. Zivny, 104 Wintergreen Hill, Painesville, Ohio 44077

[21] Appl. No.: 95,174

[22] Filed: Sep. 10, 1987

[51] Int. Cl.$^4$ ............................................. A61F 5/44
[52] U.S. Cl. ..................................... 604/353; 604/349
[58] Field of Search ............... 604/349, 350, 351, 352, 604/353, 385.1, 369, 327, 319, 322, 323, 324, 325, 326, 329, 340

[56] References Cited

U.S. PATENT DOCUMENTS

| | | | |
|---|---|---|---|
| 2,484,356 | 10/1949 | Ribeiro | 128/295 |
| 2,840,079 | 5/1956 | Conway | 128/295 |
| 2,976,869 | 3/1961 | Silverstone et al. | 604/353 |
| 3,357,430 | 12/1967 | Rosenberg | 604/353 |
| 3,397,698 | 8/1968 | Hickey | 128/295 |
| 3,405,714 | 10/1968 | Moss | 128/295 |
| 3,559,651 | 2/1971 | Moss | 128/295 |
| 3,608,552 | 9/1971 | Broerman | 128/295 |
| 3,721,243 | 3/1973 | Hesterman et al. | 604/353 |
| 3,739,783 | 6/1973 | Broerman | 128/295 |
| 4,073,295 | 2/1978 | Laufbahn | 604/353 |
| 4,387,726 | 6/1983 | Denard | 128/760 |
| 4,606,736 | 8/1986 | Van De Weghe | 604/327 |
| 4,655,759 | 4/1987 | Romans-Hess et al. | 604/385.1 |
| 4,718,899 | 1/1988 | Itoh et al. | 604/380 |

Primary Examiner—Noah P. Kamen
Attorney, Agent, or Firm—Renner, Otto, Boisselle & Sklar

[57] ABSTRACT

A sportsmans urine collection pouch having a holster support structure for containing a removable urine reservoir tube within which is a removable anti-collapse filler mesh. The pouch is securable in operating position to its user by strategically placed laces.

13 Claims, 2 Drawing Sheets

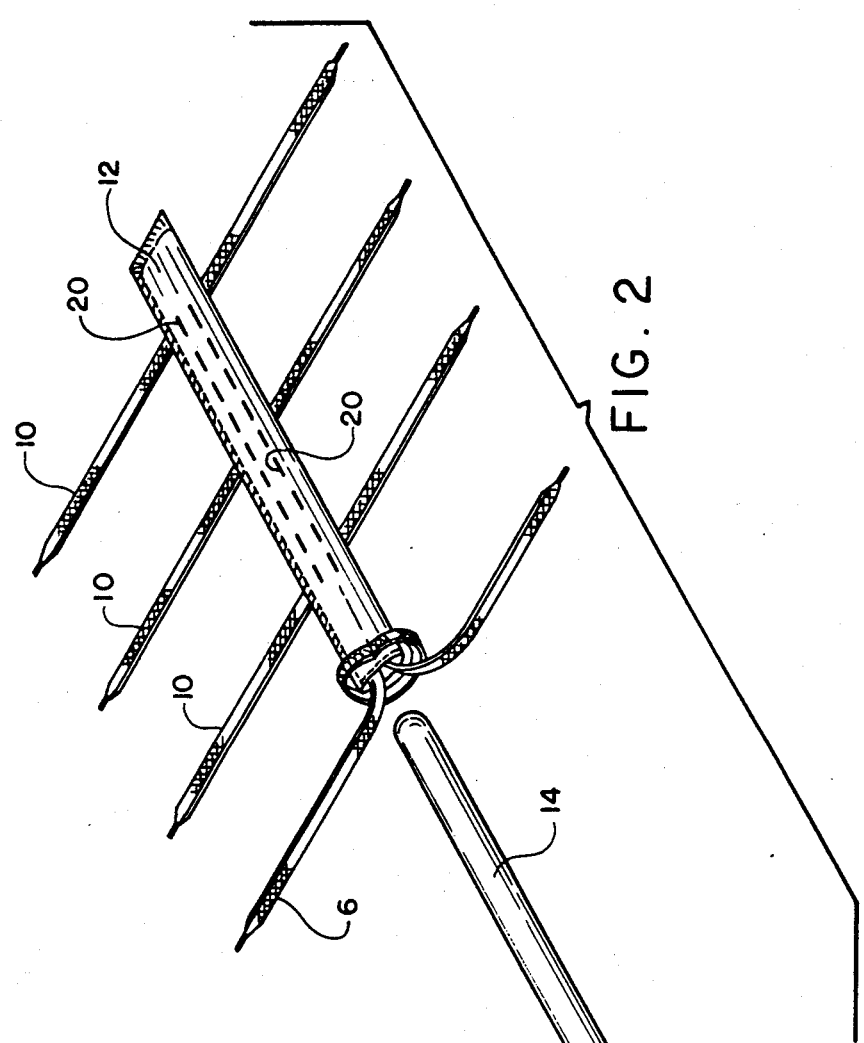
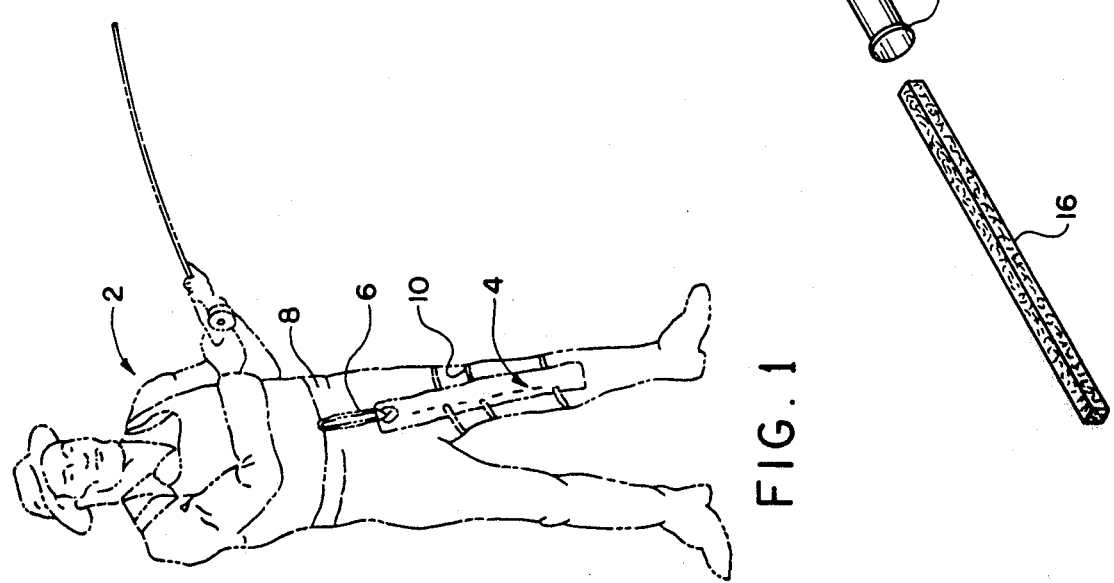

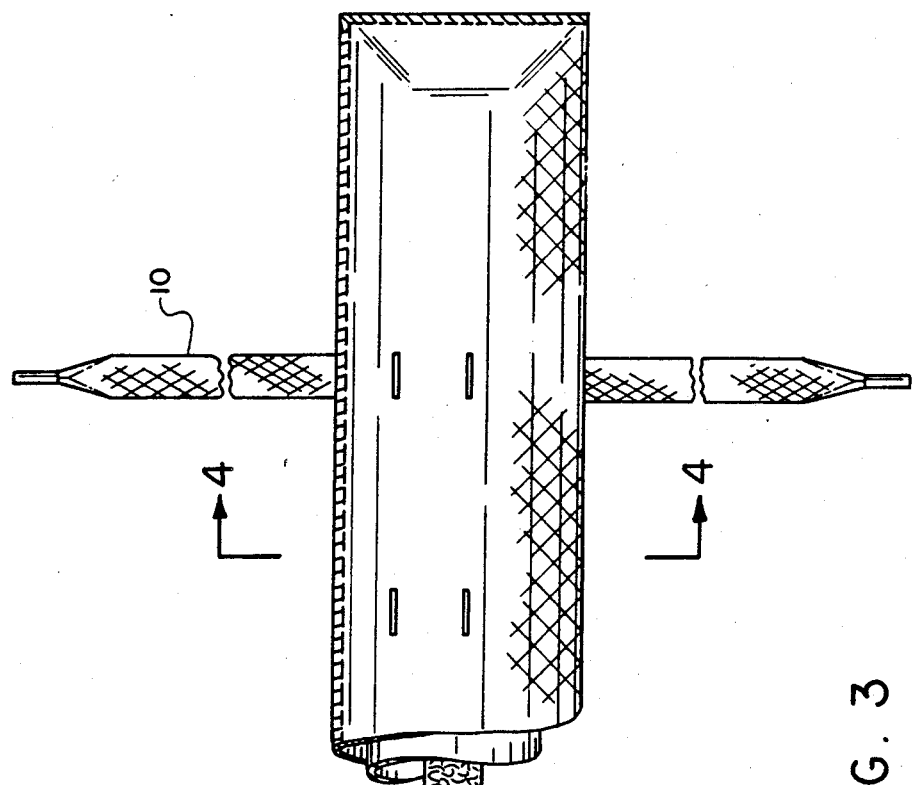
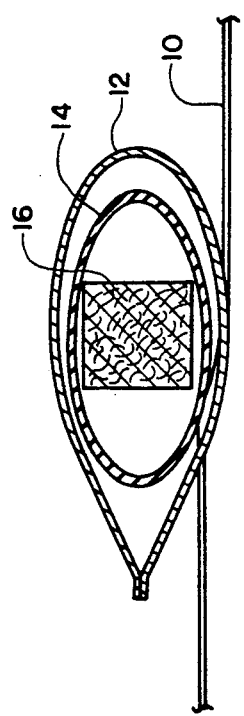
FIG. 3
FIG. 4

SPORTMAN'S REUSABLE, ANTI-COLLAPSING URINE COLLECTION DEVICE

BACKGROUND OF THE INVENTION

1. Field of the Invention.

The urine collection device exemplified by the instant invention was originally designed for use by wading fishermen. The device is particularly useful during early spring and late fall when wading in extremely cold water. The device, however, is multi-functional in that it may be used by cross-country skiers, hikers, joggers, small plane pilots, duck and deer hunters and others. The device is designed to be reusable and easily worn with bulky clothing and inside of a pair of waders. These features place the device somewhat outside the scope of products of a similar nature that had been developed for use by geriatric males or those who are chronically ill or otherwise experience some degree of incontinence.

Because of the environment in which the device is used, it is necessary to provide a pouch that will not collapse under the pressure of water that is exerting force against the outside of a wader leg when the individual using device is in a stream.

2. Description of the Prior Art.

Both male and female urine collection devices are known in the prior art. These devices, for the most part, however, have been most often found in the medical field. Most of the devices were uncomfortable to wear and did not provide the freedom of movement necessary for a sportsman.

SUMMARY OF THE INVENTION

The present invention is a urine containment pouch designed to be strapped around the leg of the user and secured in the belt area for a comfortable fit. The pouch may be conveniently worn over pants and heavy clothing and under a pair of waders. It is most useful for the wading fisherman or the hunter although, as previously mentioned, it has application in other fields of sporting endeavor as well as in situations where a bathroom or other suitable facilities are not readily available.

It is a feature of the present invention to provide a holster made of a non-irritating, non-abrasive, polished and comfortable material. Inside the holster a reservoir tube is placed for the collection of urine. Inside the reservoir tube is an anti-collapsing filler mesh made of non-toxic and non-irritating material. The filler mesh prevents the collapse of the reservoir tube when outside pressure is exerted on the pouch. Such an outside pressure condition is found when one using the device wades into streams, lakes or marshes in pursuit of his sporting endeavor.

Another feature of the device is that the holster is adapted to be worn on either leg as the user might desire. As might be imagined the device, being of somewhat a personal nature, should be adaptable to a variety of individuals. Accommodation in this respect has been provided by the instant invention. For instance, the top of the reservoir orifice is spaced from the top end of the filler mesh to allow comfortable wearing. For additional comfort it is an object of the invention to provide a rolled top end of the reservoir tube and preferably to fabricate the tube of a material such as natural rubber which provides still further comfort to the user.

Another feature of the invention is that the entire device is washable and reusable.

Further objects and features of the invention will become readily apparent upon reading the specification in conjunction with the accompanying drawings.

BRIEF DESCRIPTION OF THE DRAWINGS

FIG. 1 is a perspective view of a wading fisherman utilizing the invention;

FIG. 2 is an exploded view of the invention;

FIG. 3 is a cutaway view of the invention; and,

FIG. 4 is a cross-sectional view taken along lines 4-4 of FIG. 3.

DETAILED DESCRIPTION OF THE PREFERRED EMBODIMENT

FIG. 1 shows a fisherman 2 using the device of the present invention. As can be seen the urine collection device 4 is adapted to be strapped about the leg of a fisherman and secured at its upper portion by a strap connected to a belt worn by the user. It should be realized that in lieu of a belt, other suitable vessel attachment structures may be used.

In viewing FIG. 2 in conjunction with FIG. 1 it will be seen that a strap 6 is a lace that may readily be adjusted about the belt 8 of the wearer. Additional laces 10 are provided to facilitate securing the device about the leg of the user. It is envisioned that these straps, or laces, be made of a sturdy non-fraying material, not only for firm support of the device about the leg of a user but also to provide an extended service life.

The elements comprising the device include a holster 12, a reservoir tube 14 and an anti-collapsing structure 16. When these three elements are telescoped together as is shown in FIG. 3 the device then is ready to be secured in position for use.

As can be seen, the holster serves as a support structure for the urine containment vessel. It is presently envisioned that it be made of polished polyester felt. The material should preferably be non-staining, non-irritating, not stretchable and not shrinkable.

The reservoir tube, as has been previously mentioned, is preferably made of natural rubber so that it will be comfortable in use and so that leakage problems can be avoided. Although a number of manufacturing methods may be utilized to fabricate the tube, it quite easily can be made by a dipping process or be molded or fabricated. The tube top 15 is rolled for comfort. With further respect to the material used to make the reservoir tube, such material should be non-toxic, non-staining and non-irritating.

One of the keys to the functionality of the device is the anti-colllapsing structure which is inserted into the reservoir tube. This anti-collapsing filler mesh should be constructed of a material that is non-toxic and non-irritating. It is presently envisioned that polyurethane be used in constructing the filler mesh.

It should be appreciated that some experimentation with the device is desirable so that the user can secure it to himself in a manner that is most comfortable. The manner of attachment may vary from individual to individual and this is understandable due to the quite personal nature of the pouch. For instance, one may choose to fasten one, two or all the laces about the leg, whereas other users may prefer not to use them at all but merely rely on the top strap to secure the device to his belt.

The holster is designed such that it may be strapped to either the right or left leg and apertures 20 in the holster easily accommodate this leg to leg adjustment.

It can be appreciated that once the holster is strapped about the wearer that the reservoir tube may be easily removed from the holster, emptied, and returned to the holster for further use.

When the day's activities are over, the device may be easily cleaned, after emptying, by adding a few drops of liquid detergent to the pouch, pouring in hot water, shaking, emptying, rinsing and hanging to dry.

It will be appreciated by those skilled in the art that a readily worn reservoir which is not susceptible to collapsing or kinking during rigorous use by the outdoorsman provides extreme privacy when responding to nature's call. The device facilitates remaining in a stream at a favorite fishing spot. When used in other environments such as duck hunting or deer hunting the device permits the wearer to remain perfectly still as is often called for in such hunting situations while still being able to attend to this personal urination needs.

Having fully described my invention I wish to be restricted only by the scope of the appended claims.

I claim:

1. A reusable urine containment device comprising:
   a holster,
   a reservoir tube contained within the holster,
   means for preventing the collapse of the reservoir tube in response to outside pressure having a magnitude that a leg of a wading fisherman would experience, said anticollapse structure maintaining said magnitude even if wet, said means comprising an anti-collapse structure contained within the reservoir tube, and
   means for securing the containment device in operating position.

2. The containment device of claim 1 wherein said device is reusable and wherein said anti-collapse structure is polyurethane filler mesh.

3. The containment device of claim 1 wherein said means for securing comprises a lace which may be adjusted with respect to a device attachment structure employed by a user of the device and further comprises a lace which may be adjusted in proximity to a leg of the user.

4. The containment device of claim 1, said means for preventing the collapse of the reservoir tube being washable and reusable.

5. The device of claim 1, said tube and said means for preventing collapse of the reservoir being non-absorbent of urine coming in contact therewith such that they may be emptied of said urine.

6. The containment device of claim 1, said device being contained within the leg of a wader.

7. The device of claim 1, said device adapted for sporting and fishing applications.

8. A reusable urine collection device comprising a reservoir; a reusable, anti-collapsing apparatus contained within said reservoir; and operable to oppose an outside pressure having a magnitude that a leg of a wading fisherman would experience, said anti-collapsing apparatus maintaining said magnitude even if wet and, support means for removably containing said reservoir and anti-collapsing apparatus, said apparatus and said reservoir being adapted to be removed from said support means, emptied of urine, and returned to said support means for reuse.

9. The urine containment device of claim 8 wherein said reservoir is flexible.

10. A method of accommodating a sportsman's urination needs comprising the steps of:
    providing a reusable urine containment vessel having a reservoir, an anti-collapse structure contained within the reservoir, and operable to oppose an outside force having a magnitude that a leg of a wading fisherman would experience, said anti-collapse structure maintaining said magnitude even if wet and means for securing the containment vessel in operating position,
    placing said urine containment vessel in operating position,
    filling said reservoir,
    removing said reservoir and anti-collapse structure from operating position, emptying same, and returning them to operating position.

11. The method of claim 10 further comprising the steps of:
    placing cleaning solution in the reservoir and about the anti-collapse structure after emptying the reservoir of urine,
    shaking the reservoir,
    emptying said cleaning solution from the reservoir, and
    permitting said reservoir and anti-collapse structure to dry.

12. A sportsman's reusable, anti-collapsing urine collection device comprising a urine collection receptacle and an anti-collapsing device, said anti-collapsing device being removable from said receptacle and operable to oppose on outside force having a magnitude that a leg of a wading fisherman would experience even when said device is wet with urine.

13. The device of claim 12 further including waders, said device being contained within said waders.

* * * * *